(12) United States Patent
Xie et al.

(10) Patent No.: US 11,279,973 B2
(45) Date of Patent: Mar. 22, 2022

(54) PRIMER COMBINATION FOR DETECTING 9 NA SUBTYPE AIVS AND APPLICATION THEREOF

(71) Applicant: GUANGXI VETERINARY RESEARCH INSTITUTE, Nanning (CN)

(72) Inventors: Zhixun Xie, Nanning (CN); Sisi Luo, Nanning (CN); Jiaoling Huang, Nanning (CN); Zhiqin Xie, Nanning (CN); Liji Xie, Nanning (CN); Minxiu Zhang, Nanning (CN); Meng Li, Nanning (CN); Sheng Wang, Nanning (CN); Dan Li, Naning (CN); Tingting Zeng, Nanning (CN); Yanfang Zhang, Nanning (CN); Qing Fan, Nanning (CN); Xianwen Deng, Nanning (CN)

(73) Assignee: GUANGXI VETERINARY RESEARCH INSTITUTE, Nanning (CN)

( * ) Notice: Subject to any disclaimer, the term of this patent is extended or adjusted under 35 U.S.C. 154(b) by 0 days.

(21) Appl. No.: 16/649,078

(22) PCT Filed: Apr. 24, 2019

(86) PCT No.: PCT/CN2019/084036
§ 371 (c)(1),
(2) Date: Mar. 19, 2020

(87) PCT Pub. No.: WO2020/143132
PCT Pub. Date: Jul. 16, 2020

(65) Prior Publication Data
US 2021/0071231 A1    Mar. 11, 2021

(30) Foreign Application Priority Data
Jan. 7, 2019 (CN) .......................... 201910012094.7

(51) Int. Cl.
*C12Q 1/68* (2018.01)
*C12Q 1/686* (2018.01)
*C12Q 1/70* (2006.01)

(52) U.S. Cl.
CPC ............ *C12Q 1/686* (2013.01); *C12Q 1/701* (2013.01); *C12Q 2600/16* (2013.01)

(58) Field of Classification Search
CPC ...................................................... C12Q 1/68
(Continued)

(56) References Cited

FOREIGN PATENT DOCUMENTS

| CN | 105349697 A | * | 2/2016 | ............ C12Q 1/701 |
| CN | 109487011 | | 3/2019 | |
| CN | 109487012 | | 3/2019 | |

OTHER PUBLICATIONS

Huang et al., Neuraminidase subtyping of avian influenza viruses with PrimerHunter-designed primers and quadruplicate primer pools, PLoS One. Nov. 29, 2013;8(11):e81842. doi: 10.1371/journal.pone. 0081842. eCollection 2013.*

(Continued)

*Primary Examiner* — Aaron A Priest
(74) *Attorney, Agent, or Firm* — Hauptman Ham, LLP (57) ABSTRACT

The present invention discloses a primer combination for detecting 9 NA subtype AIVs and an application thereof. The present invention protects a primer combination comprising 10 primer pairs (20 primers), and the 20 primers are set forth in SEQ ID NO: 1 to SEQ ID NO: 20 of the Sequence Listing in sequence. When used for identifying 9 NA subtypes, a GeXP detection method in combination with the primer combination provided by the present invention has the advantages of high throughput, fast, time-saving and labor-saving. The present invention provides an effective (Continued)

method for rapid identification of 9 different NA subtype AIVs and has a broad application prospect.

5 Claims, 1 Drawing Sheet

Specification includes a Sequence Listing.

(58) Field of Classification Search
USPC .............................................................. 435/6
See application file for complete search history.

(56) References Cited

OTHER PUBLICATIONS

Sun et al., Development of a multiplex probe combination-based one-step real-time reverse transcription-PCR for NA subtype typing of avian influenza virus, Scientific Reports (Nature Publisher Group); London vol. 7, (Oct. 2017): 1-11. DOI: 10.1038/s41598-017-13768-4.*
International search report dated Oct. 9, 2019 from corresponding application No. PCT/CN2019/084036.
Office Action dated Sep. 27, 2019 from corresponding application No. CN 201910012094.7.

* cited by examiner

PRIMER COMBINATION FOR DETECTING 9 NA SUBTYPE AIVS AND APPLICATION THEREOF

RELATED APPLICATIONS

The present application is a National Phase of International Application Number PCT/CN2019/084036, filed Apr. 24, 2019, and claims the priority of China Application No. 201910012094.7, filed Jan. 7, 2019.

INCORPORATION BY REFERENCE

The sequence listing provided in the file entitled NWB1980048US_REV_SQL_2021-10-25.txt, which is an ASCII text file that was created on Oct. 25, 2021, and which comprises 5,855 bytes, is hereby incorporated by reference in its entirety.

TECHNICAL FIELD

The present invention belongs to the field of biotechnology, and particularly relates to a primer combination for detecting 9 NA subtype AIVs and its application.

BACKGROUND ART

Avian influenza virus (AIV) belongs to the orthomyxoviridae type A influenza virus. So far, 16 HA subtypes and 9 NA subtypes have been found in poultry, depending on the antigenicity of HA and NA. In recent years, the 17th and 18th HA subtypes and the 10th and 11th NA subtypes have been found in bats. In 1997, there were death cases of human infection with H5N1 subtype AIV in Hong Kong, and the epidemic broke out, making people "look pale when talking about poultry" and causing serious economic losses to the breeding industry. In recent years, cases of human infection with AIV have been reported. In 2013, H7N9 has been found infecting and killing humans in China's Yangtze river delta and spread in most parts of the country, causing 5 waves of infection. At present, there are still reports of human infection with H7N9, posing a serious threat to public health security. H10N8 and H6N1 have also been reported to infect humans for the first time. AIV is a segmented virus with 8 gene segments. Different subtypes of AIV have the ability to exchange gene segments with each other, thus producing AIV with unknown pathogenicity. Therefore, the monitoring of AIV is of great significance for the effective prevention and control of the disease, and it is necessary to establish a rapid detection method of AIV as a technical reserve. At present, in the epidemiological investigation of AIV, samples are usually collected and inoculated to SPF embryos for virus isolation. H subtype is identified by HA and HI tests, while N subtype is identified by very limited methods. The traditional method for detecting NA subtype AIV is mainly neuraminidase inhibition (NI) test, which is the gold standard test method recommended by the Office International des Epizooties, but it is time-consuming and requires specific positive serum.

The GeXP system (Gene Expression Profiler Genetic Analysis System) multiplex PCR amplification uses a combination of fluorescently labeled universal primers and specific chimeric primers (i.e., the 5' end of the gene-specific primer is linked to the universal primer sequence) to trigger multiplex system amplification. At the beginning of the PCR reaction, reverse transcription is first performed by binding the reverse-specific chimeric primer to the original template, and then the second strand of cDNA is synthesized from the forward-specific chimeric primer; after that, the specific sequences of the forward and reverse chimeric primers are used to start the PCR reaction using the cDNA as a template, and the complementary sequences of the universal primers are respectively amplified; then the fluorescently labeled universal primers, which are dominant in the reaction system, bind to their complementary sequences to trigger subsequent amplification; the universal primers and the fluorescently labeled base sequences in the reaction system are complementary, the PCR products are separated by GeXP capillary electrophoresis; the PCR products containing fluorescent labels are detected by the GeXP detection window; the length of the amplified fragment is calculated based on the migration time of the detected fragment and the standard molecular fragment (DNA Size Standard, DSS) and the intensity of the fluorescent signal represents the amplified content of the isolated fragment.

SUMMARY OF THE INVENTION

The object of the present invention is to provide a primer combination for detecting 9 NA subtype AIVs and its application.

The present invention protects a primer combination, which comprises the following 10 primer pairs:
primer pair AIV-M, which consists of a forward primer and a reverse primer, wherein the forward primer is (a1), (a2), (a3) or (a4) and the reverse primer is (b1), (b2), (b3) or (b4);
(a1) a primer with the nucleotide sequence set forth in SEQ ID NO: 1 of the Sequence Listing;
(a2) a primer with the nucleotide sequence set forth in positions 19-38 of SEQ ID NO: 1 of the Sequence Listing;
(a3) a primer comprising the following segments in order from upstream to downstream: a GeXP universal primer and a gene-specific primer;
(a4) a primer consisting of the following segments in order from upstream to downstream: a GeXP universal primer and a gene-specific primer;
wherein, the gene-specific primers in (a3) and/or (a4) have the nucleotide sequence set forth in positions 19-38 of SEQ ID NO: 1 of the Sequence Listing;
(b1) a primer with the nucleotide sequence set forth in SEQ ID NO: 2 of the Sequence Listing;
(b2) a primer with the nucleotide sequence set forth in positions 20-39 of SEQ ID NO: 2 of the Sequence Listing;
(b3) a primer comprising the following segments in order from upstream to downstream: a GeXP universal primer and a gene-specific primer;
(b4) a primer consisting of the following segments in order from upstream to downstream: a GeXP universal primer and a gene-specific primer;
wherein, the gene-specific primers in (b3) and/or (b4) have the nucleotide sequence set forth in positions 20-39 of SEQ ID NO: 2 of the Sequence Listing;
primer pair N1, which consists of a forward primer and a reverse primer, wherein the forward primer is (i1), (i2), (i3) or (i4) and the reverse primer is (j1), (j2), (j3) or (j4);
(i1) a primer with the nucleotide sequence set forth in SEQ ID NO: 3 of the Sequence Listing;
(i2) a primer with the nucleotide sequence set forth in positions 19-38 of SEQ ID NO: 3 of the Sequence Listing;
(i3) a primer comprising the following segments in order from upstream to downstream: a GeXP universal primer and a gene-specific primer;

(i4) a primer consisting of the following segments in order from upstream to downstream: a GeXP universal primer and a gene-specific primer;
wherein, the gene-specific primers in (i3) and/or (i4) have the nucleotide sequence set forth in positions 19-38 of SEQ ID NO: 3 of the Sequence Listing;
(j1) a primer with the nucleotide sequence set forth in SEQ ID NO: 4 of the Sequence Listing;
(j2) a primer with the nucleotide sequence set forth in positions 20-38 of SEQ ID NO: 4 of the Sequence Listing;
(j3) a primer comprising the following segments in order from upstream to downstream: a GeXP universal primer and a gene-specific primer;
(j4) a primer consisting of the following segments in order from upstream to downstream: a GeXP universal primer and a gene-specific primer;
wherein, the gene-specific primers in (j3) and/or (j4) have the nucleotide sequence set forth in positions 20-38 of SEQ ID NO: 4 of the Sequence Listing;
primer pair N2, which consists of a forward primer and a reverse primer, wherein the forward primer is (k1), (k2), (k3) or (k4) and the reverse primer is (l1), (l2), (l3) or (l4);
(k1) a primer with the nucleotide sequence set forth in SEQ ID NO: 5 of the Sequence Listing;
(k2) a primer with the nucleotide sequence set forth in positions 19-35 of SEQ ID NO: 5 of the Sequence Listing;
(k3) a primer comprising the following segments in order from upstream to downstream: a GeXP universal primer and a gene-specific primer;
(k4) a primer consisting of the following segments in order from upstream to downstream: a GeXP universal primer and a gene-specific primer;
wherein, the gene-specific primers in (k3) and/or (k4) have the nucleotide sequence set forth in positions 19-35 of SEQ ID NO: 5 of the Sequence Listing;
(l1) a primer with the nucleotide sequence set forth in SEQ ID NO: 6 of the Sequence Listing;
(l2) a primer with the nucleotide sequence set forth in positions 20-36 of SEQ ID NO: 6 of the Sequence Listing;
(l3) a primer comprising the following segments in order from upstream to downstream: a GeXP universal primer and a gene-specific primer;
(l4) a primer consisting of the following segments in order from upstream to downstream: a GeXP universal primer and a gene-specific primer;
wherein, the gene-specific primers in (l3) and/or (l4) have the nucleotide sequence set forth in positions 20-36 of SEQ ID NO: 6 of the Sequence Listing;
primer pair N3, which consists of a forward primer and a reverse primer, wherein the forward primer is (m1), (m2), (m3) or (m4) and the reverse primer is (n1), (n2), (n3) or (n4);
(m1) a primer with the nucleotide sequence set forth in SEQ ID NO: 7 of the Sequence Listing;
(m2) a primer with the nucleotide sequence set forth in positions 19-41 of SEQ ID NO: 7 of the Sequence Listing;
(m3) a primer comprising the following segments in order from upstream to downstream: a GeXP universal primer and a gene-specific primer;
(m4) a primer consisting of the following segments in order from upstream to downstream: a GeXP universal primer and a gene-specific primer;
wherein, the gene-specific primers in (m3) and/or (m4) have the nucleotide sequence set forth in positions 19-41 of SEQ ID NO: 7 of the Sequence Listing;
(n1) a primer with the nucleotide sequence set forth in SEQ ID NO: 8 of the Sequence Listing;
(n2) a primer with the nucleotide sequence set forth in positions 20-41 of SEQ ID NO: 8 of the Sequence Listing;
(n3) a primer comprising the following segments in order from upstream to downstream: a GeXP universal primer and a gene-specific primer;
(n4) a primer consisting of the following segments in order from upstream to downstream: a GeXP universal primer and a gene-specific primer;
wherein, the gene-specific primers in (n3) and/or (n4) have the nucleotide sequence set forth in positions 20-41 of SEQ ID NO: 8 of the Sequence Listing;
primer pair N4, which consists of a forward primer and a reverse primer, wherein the forward primer is (o1), (o2), (o3) or (o4) and the reverse primer is (p1), (p2), (p3) or (p4);
(o1) a primer with the nucleotide sequence set forth in SEQ ID NO: 9 of the Sequence Listing;
(o2) a primer with the nucleotide sequence set forth in positions 19-40 of SEQ ID NO: 9 of the Sequence Listing;
(o3) a primer comprising the following segments in order from upstream to downstream: a GeXP universal primer and a gene-specific primer;
(o4) a primer consisting of the following segments in order from upstream to downstream: a GeXP universal primer and a gene-specific primer;
wherein, the gene-specific primers in (o3) and/or (o4) have the nucleotide sequence set forth in positions 19-40 of SEQ ID NO: 9 of the Sequence Listing;
(p1) a primer with the nucleotide sequence set forth in SEQ ID NO: 10 of the Sequence Listing;
(p2) a primer with the nucleotide sequence set forth in positions 20-39 of SEQ ID NO: 10 of the Sequence Listing;
(p3) a primer comprising the following segments in order from upstream to downstream: a GeXP universal primer and a gene-specific primer;
(p4) a primer consisting of the following segments in order from upstream to downstream:
a GeXP universal primer and a gene-specific primer;
wherein, the gene-specific primers in (p3) and/or (p4) have the nucleotide sequence set forth in positions 20-39 of SEQ ID NO: 10 of the Sequence Listing;
primer pair N5, which consists of a forward primer and a reverse primer, wherein the forward primer is (q1), (q2), (q3) or (q4) and the reverse primer is (r1), (r2), (r3) or (r4);
(q1) a primer with the nucleotide sequence set forth in SEQ ID NO: 11 of the Sequence Listing;
(q2) a primer with the nucleotide sequence set forth in positions 19-38 of SEQ ID NO: 11 of the Sequence Listing;
(q3) a primer comprising the following segments in order from upstream to downstream: a GeXP universal primer and a gene-specific primer;
(q4) a primer consisting of the following segments in order from upstream to downstream: a GeXP universal primer and a gene-specific primer;
wherein, the gene-specific primers in (q3) and/or (q4) have the nucleotide sequence set forth in positions 19-38 of SEQ ID NO: 11 of the Sequence Listing;
(r1) a primer with the nucleotide sequence set forth in SEQ ID NO: 12 of the Sequence Listing;
(r2) a primer with the nucleotide sequence set forth in positions 20-40 of SEQ ID NO: 12 of the Sequence Listing;
(r3) a primer comprising the following segments in order from upstream to downstream: a GeXP universal primer and a gene-specific primer;
(r4) a primer consisting of the following segments in order from upstream to downstream: a GeXP universal primer and a gene-specific primer;

wherein, the gene-specific primers in (r3) and/or (r4) have the nucleotide sequence set forth in positions 20-40 of SEQ ID NO: 12 of the Sequence Listing;

primer pair N6, which consists of a forward primer and a reverse primer, wherein the forward primer is (s1), (s2), (s3) or (s4) and the reverse primer is (t1), (t2), (t3) or (t4);

(s1) a primer with the nucleotide sequence set forth in SEQ ID NO: 13 of the Sequence Listing;

(s2) a primer with the nucleotide sequence set forth in positions 19-43 of SEQ ID NO: 13 of the Sequence Listing;

(s3) a primer comprising the following segments in order from upstream to downstream: a GeXP universal primer and a gene-specific primer;

(s4) a primer consisting of the following segments in order from upstream to downstream: a GeXP universal primer and a gene-specific primer;

wherein, the gene-specific primers in (s3) and/or (s4) have the nucleotide sequence set forth in positions 19-43 of SEQ ID NO: 13 of the Sequence Listing;

(t1) a primer with the nucleotide sequence set forth in SEQ ID NO: 14 of the Sequence Listing;

(t2) a primer with the nucleotide sequence set forth in positions 20-44 of SEQ ID NO: 14 of the Sequence Listing;

(t3) a primer comprising the following segments in order from upstream to downstream: a GeXP universal primer and a gene-specific primer;

(t4) a primer consisting of the following segments in order from upstream to downstream: a GeXP universal primer and a gene-specific primer;

wherein, the gene-specific primers in (t3) and/or (t4) have the nucleotide sequence set forth in positions 20-44 of SEQ ID NO: 14 of the Sequence Listing;

primer pair N7, which consists of a forward primer and a reverse primer, wherein the forward primer is (u1), (u2), (u3) or (u4) and the reverse primer is (v1), (v2), (v3) or (v4);

(u1) a primer with the nucleotide sequence set forth in SEQ ID NO: 15 of the Sequence Listing;

(u2) a primer with the nucleotide sequence set forth in positions 19-38 of SEQ ID NO: 15 of the Sequence Listing;

(u3) a primer comprising the following segments in order from upstream to downstream: a GeXP universal primer and a gene-specific primer;

(u4) a primer consisting of the following segments in order from upstream to downstream: a GeXP universal primer and a gene-specific primer;

wherein, the gene-specific primers in (u3) and/or (u4) have the nucleotide sequence set forth in positions 19-38 of SEQ ID NO: 15 of the Sequence Listing;

(v1) a primer with the nucleotide sequence set forth in SEQ ID NO: 16 of the Sequence Listing;

(v2) a primer with the nucleotide sequence set forth in positions 20-39 of SEQ ID NO: 16 of the Sequence Listing;

(v3) a primer comprising the following segments in order from upstream to downstream: a GeXP universal primer and a gene-specific primer;

(v4) a primer consisting of the following segments in order from upstream to downstream: a GeXP universal primer and a gene-specific primer;

wherein, the gene-specific primers in (v3) and/or (v4) have the nucleotide sequence set forth in positions 20-39 of SEQ ID NO: 16 of the Sequence Listing;

primer pair N8, which consists of a forward primer and a reverse primer, wherein the forward primer is (w1), (w2), (w3) or (w4) and the reverse primer is (x1), (x2), (x3) or (x4);

(w1) a primer with the nucleotide sequence set forth in SEQ ID NO: 17 of the Sequence Listing;

(w2) a primer with the nucleotide sequence set forth in positions 19-38 of SEQ ID NO: 17 of the Sequence Listing;

(w3) a primer comprising the following segments in order from upstream to downstream: a GeXP universal primer and a gene-specific primer;

(w4) a primer consisting of the following segments in order from upstream to downstream: a GeXP universal primer and a gene-specific primer;

wherein, the gene-specific primers in (w3) and/or (w4) have the nucleotide sequence set forth in positions 19-38 of SEQ ID NO: 17 of the Sequence Listing;

(x1) a primer with the nucleotide sequence set forth in SEQ ID NO: 18 of the Sequence Listing;

(x2) a primer with the nucleotide sequence set forth in positions 20-40 of SEQ ID NO: 18 of the Sequence Listing;

(x3) a primer comprising the following segments in order from upstream to downstream: a GeXP universal primer and a gene-specific primer;

(x4) a primer consisting of the following segments in order from upstream to downstream: a GeXP universal primer and a gene-specific primer;

wherein, the gene-specific primers in (x3) and/or (x4) have the nucleotide sequence set forth in positions 20-40 of SEQ ID NO: 18 of the Sequence Listing;

primer pair N9, which consists of a forward primer and a reverse primer, wherein the forward primer is (y1), (y2), (y3) or (y4) and the reverse primer is (z1), (z2), (z3) or (z4);

(y1) a primer with the nucleotide sequence set forth in SEQ ID NO: 19 of the Sequence Listing;

(y2) a primer with the nucleotide sequence set forth in positions 19-39 of SEQ ID NO: 19 of the Sequence Listing;

(y3) a primer comprising the following segments in order from upstream to downstream: a GeXP universal primer and a gene-specific primer;

(y4) a primer consisting of the following segments in order from upstream to downstream: a GeXP universal primer and a gene-specific primer;

wherein, the gene-specific primers in (y3) and/or (y4) have the nucleotide sequence set forth in positions 19-39 of SEQ ID NO: 19 of the Sequence Listing;

(z1) a primer with the nucleotide sequence set forth in SEQ ID NO: 20 of the Sequence Listing;

(z2) a primer with the nucleotide sequence set forth in positions 20-39 of SEQ ID NO: 20 of the Sequence Listing;

(z3) a primer comprising the following segments in order from upstream to downstream: a GeXP universal primer and a gene-specific primer;

(z4) a primer consisting of the following segments in order from upstream to downstream: a GeXP universal primer and a gene-specific primer;

wherein, the gene-specific primers in (z3) and/or (z4) have the nucleotide sequence set forth in positions 20-39 of SEQ ID NO: 20 of the Sequence Listing.

In the primer combination, the molar quantities of various primers are equal.

The primer combination consists of the above 10 primer pairs.

The present invention further protects use of the primer combination for the following (I), (II), (III), (IV), (V), (VI), (VII) or (VII):

(I) identifying the N subtype to which an avian influenza virus to be tested belongs;

(II) identifying whether an virus to be tested is an avian influenza virus, and if it is an avian influenza virus, identifying the N subtype to which it belongs;

(III) identifying the N subtype to which an avian influenza virus contained in a sample to be tested belongs;

(IV) identifying whether a sample to be tested contains an avian influenza virus, and if it contains an avian influenza virus, identifying the N subtype to which the contained avian influenza virus belongs;

(V) preparing a kit; the function of the kit is to identify the N subtype to which an avian influenza virus to be tested belongs;

(VI) preparing a kit; the function of the kit is to identify whether an virus to be tested is an avian influenza virus, and if it is an avian influenza virus, identify the N subtype to which it belongs;

(VII) preparing a kit; the function of the kit is to identify the N subtype to which an avian influenza virus contained in a sample to be tested belongs;

(VIII) preparing a kit; the function of the kit is to identify whether a sample to be tested contains an avian influenza virus, and if it contains an avian influenza virus, identify the N subtype to which the contained avian influenza virus belongs.

In the above use, the N subtype is N1 subtype, N2 subtype, N3 subtype, N4 subtype, N5 subtype, N6 subtype, N7 subtype, N8 subtype, or N9 subtype.

The present invention further protects a kit containing the primer combination; the function of the kit is the following (I), (II), (III) or (IV):

(I) identifying the N subtype to which an avian influenza virus to be tested belongs;

(II) identifying whether an virus to be tested is an avian influenza virus, and if it is an avian influenza virus, identifying the N subtype to which it belongs;

(III) identifying the N subtype to which an avian influenza virus contained in a sample to be tested belongs;

(IV) identifying whether a sample to be tested contains an avian influenza virus, and if it contains an avian influenza virus, identifying the N subtype to which the contained avian influenza virus belongs.

In the above kit, the N subtype is N1 subtype, N2 subtype, N3 subtype, N4 subtype, N5 subtype, N6 subtype, N7 subtype, N8 subtype, or N9 subtype.

The present invention further protects a preparation method of the kit, comprising the step of mixing and packaging all the primers.

The present invention further protects a method comprising the following steps: performing GeXP multiplex PCR with the cDNA of a virus to be tested as a template and the primer combination, and then conducting detection and analysis using GeXP System; if a peak in the range of 163 bp±3 bp is shown, the virus to be tested is an avian influenza virus;

if a peak in the range of 249 bp±3 bp is shown, the virus to be tested is N1 subtype avian influenza virus;

if a peak in the range of 285 bp±3 bp is shown, the virus to be tested is N2 subtype avian influenza virus;

if a peak in the range of 220 bp±3 bp is shown, the virus to be tested is N3 subtype avian influenza virus;

if a peak in the range of 152 bp±3 bp is shown, the virus to be tested is N4 subtype avian influenza virus;

if a peak in the range of 300 bp±3 bp is shown, the virus to be tested is N5 subtype avian influenza virus;

if a peak in the range of 240 bp±3 bp is shown, the virus to be tested is N6 subtype avian influenza virus;

if a peak in the range of 198 bp±3 bp is shown, the virus to be tested is N7 subtype avian influenza virus;

if a peak in the range of 177 bp±3 bp is shown, the virus to be tested is N8 subtype avian influenza virus;

if a peak in the range of 210 bp±3 bp is shown, the virus to be tested is N9 subtype avian influenza virus;

the purpose of the method is to identify whether a virus to be tested is an avian influenza virus and, if it is an avian influenza virus, identify the N subtype to which it belongs.

The present invention further protects a method comprising the following steps: performing GeXP multiplex PCR with the cDNA of a sample to be tested as a template and the primer combination, and then conducting detection and analysis using GeXP System; if a peak in the range of 163 bp±3 bp is shown, the sample to be tested contains an avian influenza virus;

if a peak in the range of 249 bp±3 bp is shown, the sample to be tested contains N1 subtype avian influenza virus;

if a peak in the range of 285 bp±3 bp is shown, the sample to be tested contains N2 subtype avian influenza virus;

if a peak in the range of 220 bp±3 bp is shown, the sample to be tested contains N3 subtype avian influenza virus;

if a peak in the range of 152 bp±3 bp is shown, the sample to be tested contains N4 subtype avian influenza virus;

if a peak in the range of 300 bp±3 bp is shown, the sample to be tested contains N5 subtype avian influenza virus;

if a peak in the range of 240 bp±3 bp is shown, the sample to be tested contains N6 subtype avian influenza virus;

if a peak in the range of 198 bp±3 bp is shown, the sample to be tested contains N7 subtype avian influenza virus;

if a peak in the range of 177 bp±3 bp is shown, the sample to be tested contains N8 subtype avian influenza virus;

if a peak in the range of 210 bp±3 bp is shown, the sample to be tested contains N9 subtype avian influenza virus;

the purpose of the method is to identify whether a sample to be tested contains an avian influenza virus, and if it contains an avian influenza virus, identify the N subtype to which the contained avian influenza virus belongs.

DETAILED DESCRIPTION OF THE INVENTION

The following examples facilitate a better understanding of the present invention, but do not limit the present invention. Unless otherwise specified, the experimental methods in the following examples are conventional methods. Unless otherwise specified, the test materials used in the following examples were purchased from stores selling conventional biochemical reagents. The quantitative experiments in the following examples were all repeated three times, and the results were averaged.

RNA/DNA co-extraction kit: TaKaRa Biotechnology (Dalian) Co., Ltd. GeXP System is a product from Beckman Coulter, Inc. GeXP START Kit, Capillary Array, Loading Buffer, DNA size standard Kit-400 Base Pairs, Separating Buffer and Separating Gel are all AB Sciex products. Nano-Drop ND-1000 nucleic acid micro-detector is a product from Thermo Fisher Scientific.

Example 1. Acquisition and Preparation of Primers

Through a large number of sequence analysis, primer design, primer verification and primer screening, 10 primer pairs were obtained. Primer pair AIV-M consists of a forward primer (SEQ ID NO: 1 in the Sequence Listing) and a reverse primer (SEQ ID NO: 2 in the Sequence Listing), and is used for identifying an avian influenza virus. Primer pair N1 consists of a forward primer (SEQ ID NO: 3 in the Sequence Listing) and a reverse primer (SEQ ID NO: 4 in the Sequence Listing), and is used for identifying N1 subtype avian influenza virus. Primer pair N2 consists of a forward primer (SEQ ID NO: 5 in the Sequence Listing) and a reverse primer (SEQ ID NO: 6 in the Sequence Listing), and is used for identifying N2 subtype avian influenza virus. Primer pair N3 consists of a forward primer (SEQ ID NO: 7 in the Sequence Listing) and a reverse primer (SEQ ID NO: 8 in the Sequence Listing), and is used for identifying N3 subtype avian influenza virus. Primer pair N4 consists of a forward primer (SEQ ID NO: 9 in the Sequence Listing) and a reverse primer (SEQ ID NO: 10 in the Sequence Listing), and is used for identifying N4 subtype avian influenza virus. Primer pair N5 consists of a forward primer (SEQ ID NO: 11 in the Sequence Listing) and a reverse primer (SEQ ID NO: 12 in the Sequence Listing), and is used for identifying N5 subtype avian influenza virus. Primer pair N6 consists of a forward primer (SEQ ID NO: 13 in the Sequence Listing) and a reverse primer (SEQ ID NO: 14 in the Sequence Listing), and is used for identifying N6 subtype avian influenza virus. Primer pair N7 consists of a forward primer (SEQ ID NO: 15 in the Sequence Listing) and a reverse primer (SEQ ID NO: 16 in the Sequence Listing), and is used for identifying N7 subtype avian influenza virus. Primer pair N8 consists of a forward primer (SEQ ID NO: 17 in the Sequence Listing) and a reverse primer (SEQ ID NO: 18 in the Sequence Listing), and is used for identifying N8 subtype avian influenza virus. Primer pair N9 consists of a forward primer (SEQ ID NO: 19 in the Sequence Listing) and a reverse primer (SEQ ID NO: 20 in the Sequence Listing), and is used for identifying N9 subtype avian influenza virus.

The nucleotide sequence of each primer and the size of the amplified fragment of each primer pair are shown in Table 1. All forward primers have the same GeXP universal primer (underlined). All reverse primers have the same GeXP universal primer (underlined).

TABLE 1

| Virus | Forward primer (5'→3') | Reverse primer (5'→3') | Amplified fragment (bp) |
| --- | --- | --- | --- |
| AIV-M | AGGTGACACTATAGAATAAGGCTCTCATGGAGTGGCTA | GTACGACTCACTATAGGGATGGACAAAGCGTCTACGCTG | 163 |
| N1 | AGGTGACACTATAGAATAGGTGTTTGGATCGGRAGAAC | GTACGACTCACTATAGGGATCAACCCAGAARCAAGGTC | 249 |
| N2 | AGGTGACACTATAGAATATTGGGTGTTCCGTTTCA | GTACGACTCACTATAGGGACCATCCGTCATTACTAC | 285 |
| N3 | AGGTGACACTATAGAATATTCCCAATAGGAACAGCYCCAGT | GTACGACTCACTATAGGGATTCTCCATGATTTRATGGAGTC | 220 |
| N4 | AGGTGACACTATAGAATACAGAYAAGGAYTCAAATGGTGT | GTACGACTCACTATAGGGACATGGTACAGTGCAATTCCT | 152 |
| N5 | AGGTGACACTATAGAATAGTGAGGTCATGGAGAAAGCA | GTACGACTCACTATAGGGATGGYCTATTCATTCCRTTCCA | 300 |
| N6 | AGGTGACACTATAGAATACACTATAGATCCYGARATGATGACC | GTACGACTCACTATAGGGAGGAGTCTTTGCTAATWGTCCTTCCA | 240 |
| N7 | AGGTGACACTATAGAATAGACAGRACWGCTTTCAGAGG | GTACGACTCACTATAGGGAGTTGCGTTGTCATTATTTCC | 198 |
| N8 | AGGTGACACTATAGAATAAGGGAATACAATGAAACAGT | GTACGACTCACTATAGGGATGCAAAACCCTTAGCATCACA | 177 |
| N9 | AGGTGACACTATAGAATACGCCCTGATAAGCTGGCCACT | GTACGACTCACTATAGGGAACAGGCCTTCTGTTGTACCA | 210 |

In Table 1, R represents A or G, Y represents C or T, and W represents A or T. In Table 1, *, according to the actually detected strains and the errors of the GeXP system such as GenomeLab™ GeXP GeneticAnalysis System capillary electrophoresis instrument, the actual amplification length detected using the above primer pair may fluctuate by 3 bp above or below the predicted length of the amplification product.

Each primer was artificially synthesized.

Example 2. Specificity of Each Primer Pair

I. Preparation of Template
1. Viral RNA Extraction and cDNA Acquisition
① Viral RNA Extraction The EasyPure Viral DNA/RNA Kit (TransGen Biotech, catalog number: ER201) was used to respectively extract RNA from the chick embryo allantoic fluid of the following virus strains, according to the kit instructions (RNA extracted from negative chick embryo allantoic fluid was used as a negative control sample): Avian influenza virus strains: A/Sparrow/Guangxi/GXs-1/2012 (H1N2 subtype), A/Chicken/GuangXi/DX/2008 (H9N2 subtype), A/Duck/GuangXi/N42/2009 (H3N2 subtype), A/Duck/HK/77/76 (H2N3 subtype), A/Duck/HK/876/80 (H10N3 subtype), A/Turkey/Ontario/6118/68 (H8N4 subtype), A/Duck/Guangxi/GXd-1/2009 (H6N5 subtype), A/Duck/HK/862/80 (H12N5 subtype), A/Duck/Guangxi/070D/2010 (H4N6 subtype), A/Duck/Guangxi/GXd-6/2010 (H6N8 subtype), A/Duck/PA/2099/12 (H11N9 subtype), A/Gull/Md/704/77 (H13N5 subtype), A/Mallard/Astrakhan/263/82 (H14N5 subtype), A/shearwater/Western Australia/2576/79 (H15N9 subtype), A/shorebird/Delaware/168/06 (H16N3 subtype) and Newcastle disease virus strain (NDV) F48, Infectious bronchitis virus strain (IBV) M41 (recorded in the following literature. LUO Si-si, XIE Zhi-xun, XIE Li-ji, et al. Visual Detection of H7 and N9 Subtypes Avian Influenza Viruses by Reverse Transcription Loop-mediated Isothermal Amplification Assay [J]. Acta Veterinaria et Zootechnica Sinica. 2015, 46(7): 1176-1183); Avian influenza virus strain: A/duck/Guangxi/GXd-5/2010 (H6N1 subtype) (recorded in the following literature: LUO Si-si, XIE Zhi-xun, ZHOU Chen-yu, et al. Isolation, Identification and Biological Characteristics Analysis of H6 Subtype Avian Influenza Virus [J]. China Poultry, 2015, 37(2): 54-56); Avian influenza virus strain: A/pigeon/Guangxi/020P/2009 (H3N6 subtype) (recorded in the following literature: Tingting Liu, Zhixun Xie, Guoli Wang, et al. Avian Influenza Virus with Hemagglutinin-Neuraminidase Combination H3N6, Isolated from a Domestic Pigeon in Guangxi, Southern China [J]. Genome Announc, 2015 Feb. 5; 3(1). pii: e01537-14. ); Avian reovirus S1133 strain (recorded in the following literature: ZHANG Kun-li, XIE Zhi-xun, HUANG Li, et al. The dynamic change of IL-17, IL-18 and IFN-γ mRNA transcription level in chicken embryo fibroblast infected with avian reovirus [J]. 2015, 35(3): 345-349).

② cDNA Acquisition

The RNA samples obtained in step ① were respectively reverse transcribed, according to the following reaction system (50 μL) and reaction conditions to obtain cDNA; DEPC water was used as a negative control.

35 μL of RNA and 1.4 μL of 50 μmol Random Primer (9 mer) were reacted at 70° C. for 10 min, the resulting solution was immediately cooled in an ice bath for 5 min and then 10 μL of 5×Reverse Transcriptase Buffer, 2 μL of 10 mM dNTP Mixture, 0.6 μL of 40 U/μL Ribonuclease Inhibitor and 1 μL of 200 U/μL M-MLV ReverseTranscriptase were added.

The reverse transcription reagents Random Primer (9mer), dNTP Mixture, Ribonuclease Inhibitor, and M-MLV Reverse Transcriptase were all purchased from TaKaRa Biotechnology (Dalian) Co., Ltd., with catalog numbers D3802, D4019, D2313A, and D2641A, respectively.

Reaction conditions: 42° C. for 1h, store at −20° C.

2. Avian influenza virus strains A/Chicken/QT35/98 (H5N9 subtype), A/Duck/42846/07 (H7N7 subtype), H7N9 field samples (H7N9 subtype), Duck/HK/47/76 (H7N2 subtype), Duck/Guangxi/1/04 (H5N1 subtype) are samples retained in the form of cDNA and have been confirmed by HA gene sequencing (H5N9, H7N7 and H7N9 are recorded in the following literature: LUO Si-si, XIE Zhi-xun, XTE Li-ji, et al. Visual Detection of H7 and N9 Subtypes Avian Influenza Viruses by Reverse Transcription Loop-mediated Isothermal Amplification Assay [J]. Acta Veterinaria et Zootechnica Sinica. 2015, 46(7): 1176-1183; H5N1 and H7N2 are recorded in the following literature: Zhixun Xie, Yaoshan Pang, Jiabo Liu, et al. A multiplex RT-PCR for detection of type A influenza virus and differentiation of avian H5, H7, and H9 hemagglutinin subtypes [J]. Molecular and Cellular Probes, 2006, 20 (3-4): 245-249).

II. The cDNA Obtained in Step I was Taken as the Template, GeXP Single-Plex PCR was Performed with the Test Primer Pairs and then GeXP System (GeXP Capillary Electrophoresis System) was Used for Detection and Analysis.

The test primer pairs: each primer pair prepared in Example 1.

Reaction system (20 μL): 4 μL of 5×PCR Buffer, 2 μL of primer solution, 4 μL of 25 mM $MgCl_2$ aqueous solution, 1 μL of JumpStart Taq DNA Polymerase, 2 μL of template cDNA, and $dH_2O$ was added up to 20 μL.

5×PCR Buffer containing GeXP universal primer pair was purchased from SCIEX, with catalog number A85017. JumpStart Taq DNA Polymerase was purchased from Sigma, with catalog number D4184.

The primer solution provided two active ingredients, i.e. the forward primer and the reverse primer of the test primer pair. In the reaction system, the final concentration of the forward primer was 20 nM, the final concentration of the reverse primer was 20 nM, the content of JumpStart Taq DNA Polymerase was 2.5 U, and the content of template cDNA was 1 pg-10 pg.

Reaction procedure: 95° C. for 5 min; 35 cycles of 95° C. for 30s, 50° C. for 30s and 72° C. for 40s; 72° C. for 8 min.

The primer pair AIV-M showed a 163 bp target peak for all subtypes of avian influenza viruses. The primer pair AIV-M did not achieve effective amplification for Newcastle disease virus, infectious bronchitis virus and avian reovirus, and no peak was observed.

The primer pair NI achieved specific amplification for the H6N1 subtype avian influenza virus and the H5N1 subtype avian influenza virus, both showing a 249 bp target peak. The primer pair N1 did not achieve effective amplification for the other viruses, and no peak was observed.

The primer pair N2 achieved specific amplification for the H1N2 subtype avian influenza virus, the H9N2 subtype avian influenza virus, the H3N2 subtype avian influenza virus and the H7N2 subtype avian influenza virus, all showing a 285 bp target peak. The primer pair N2 did not achieve effective amplification for the other viruses, and no peak was observed.

The primer pair N3 achieved specific amplification for the H2N3 subtype avian influenza virus, the H10N3 subtype avian influenza virus and the H16N3 subtype avian influenza virus, showing a 220 bp target peak. The primer pair N3 did not achieve effective amplification for the other viruses, and no peak was observed.

The primer pair N4 achieved specific amplification for the H8N4 subtype avian influenza virus, showing a 152 bp target peak. The primer pair N4 did not achieve effective amplification for the other viruses, and no peak was observed.

The primer pair N5 achieved specific amplification for the H6N5 subtype avian influenza virus, the H12N5 subtype avian influenza virus, the H13N5 subtype avian influenza virus and the H14N5 subtype avian influenza virus, showing a 300 bp target peak. The primer pair N5 did not achieve effective amplification for the other viruses, and no peak was observed.

The primer pair N6 achieved specific amplification for the H4N6 subtype avian influenza virus and the H3N6 subtype avian influenza virus, showing a 240 bp target peak. The primer pair N6 did not achieve efficient amplification for the other viruses, and no peak was observed.

The primer pair N7 achieved specific amplification for the H7N7 subtype avian influenza virus, showing a 198 bp target peak. The primer pair N7 did not achieve effective amplification for the other viruses, and no peak was observed.

The primer pair N8 achieved specific amplification for the H6N8 subtype avian influenza virus, showing a 177 bp target peak. The primer pair N8 did not achieve effective amplification for the other viruses, and no peak was observed.

The primer pair N9 achieved specific amplification for the H11N9 subtype avian influenza virus, the H15N9 subtype avian influenza virus, the H5N9 subtype avian influenza virus and the H7N9 subtype avian influenza virus, showing a 210 bp target peak. The primer pair N9 did not achieve effective amplification for the other viruses, and no peak was observed.

The results showed that the 10 primer pairs all specifically amplified the target virus, but did not cross-amplify the other viruses.

Example 3. Specificity of Primer Combination

1. Preparation of Template
The step was the same as step I of Example 2.
II. The cDNA Obtained in Step I was Taken as the Template, GeXP Multiplex PCR was Performed with the Test Primer Pairs and then GeXP System (GeXP Capillary Electrophoresis System) was Used for Detection and Analysis.

The primer combination consisted of the 10 primer pairs designed in Example 1.

Reaction system (20 μL): 4 μL of GenomeLab GeXP Start Kit 5×PCR Buffer, 2 μL of primer combination solution, 4 μL of 25 mM $MgCl_2$ aqueous solution, 1 μL of Taq DNA Polymerase, 2 μL of template cDNA, and $dH_2O$ was added up to 20 μL.

GenomeLab GeXP Start Kit 5×PCR Buffer containing GeXP universal primer pair was purchased from SCIEX, with catalog number A85017.

The primer combination solution provides the 10 primer pairs described. In the reaction system, the final concentration of each forward primer was 20 nM, the final concentration of each reverse primer was 20 nM, the content of Taq DNA Polymerase was 2.5U, and the content of template cDNA was 1 pg-10 pg.

The reaction procedure was the same as in Example 2.

For Newcastle disease virus, infectious bronchitis virus and avian reovirus, the primer combination did not achieve effective amplification, and no peak was observed.

For the H1N2 subtype avian influenza virus, the primer combination achieved specific amplification, showing a 163 bp target peak (corresponding to the primer pair AIV-M) and a 285 bp target peak (corresponding to the primer pair N2).

For the H9N2 subtype avian influenza virus, the primer combination achieved specific amplification, showing a 163 bp target peak (corresponding to the primer pair AIV-M) and a 285 bp target peak (corresponding to the primer pair N2).

For the H3N2 subtype avian influenza virus, the primer combination achieved specific amplification, showing a 163 bp target peak (corresponding to the primer pair AIV-M) and a 285 bp target peak (corresponding to the primer pair N2).

For the H2N3 subtype avian influenza virus, the primer combination achieved specific amplification, showing a 163 bp target peak (corresponding to the primer pair AIV-M) and a 220 bp target peak (corresponding to the primer pair N3).

For the H10N3 subtype avian influenza virus, the primer combination achieved specific amplification, showing a 163 bp target peak (corresponding to the primer pair AIV-M) and a 220 bp target peak (corresponding to the primer pair N3).

For the H8N4 subtype avian influenza virus, the primer combination achieved specific amplification, showing a 163 bp target peak (corresponding to the primer pair AIV-M) and a 152 bp target peak (corresponding to the primer pair N4).

For the H6N5 subtype avian influenza virus, the primer combination achieved specific amplification, showing a 163 bp target peak (corresponding to the primer pair AIV-M) and a 300 bp target peak (corresponding to the primer pair N5).

For the H12N5 subtype avian influenza virus, the primer combination achieved specific amplification, showing a 163 bp target peak (corresponding to the primer pair AIV-M) and a 300 bp target peak (corresponding to the primer pair N5).

For the H4N6 subtype avian influenza virus, the primer combination achieved specific amplification, showing a 163 bp target peak (corresponding to the primer pair AIV-M) and a 240 bp target peak (corresponding to the primer pair N6).

For the H6N8 subtype avian influenza virus, the primer combination achieved specific amplification, showing a 163 bp target peak (corresponding to the primer pair AIV-M) and a 177 bp target peak (corresponding to the primer pair N8).

For the H11N9 subtype avian influenza virus, the primer combination achieved specific amplification, showing a 163 bp target peak (corresponding to the primer pair AIV-M) and a 210 bp target peak (corresponding to the primer pair N9).

For the H13N5 subtype avian influenza virus, the primer combination achieved specific amplification, showing a 163 bp target peak (corresponding to the primer pair AIV-M) and a 300 bp target peak (corresponding to the primer pair N5).

For the H14N5 subtype avian influenza virus, the primer combination achieved specific amplification, showing a 163 bp target peak (corresponding to the primer pair AIV-M) and a 300 bp target peak (corresponding to the primer pair N5).

For the H15N9 subtype avian influenza virus, the primer combination achieved specific amplification, showing a 163 bp target peak (corresponding to the primer pair AIV-M) and a 210 bp target peak (corresponding to the primer pair N9).

For the H16N3 subtype avian influenza virus, the primer combination achieved specific amplification, showing a 163 bp target peak (corresponding to the primer pair AIV-M) and a 220 bp target peak (corresponding to the primer pair N3).

For H6N1 subtype avian influenza virus, the primer combination achieved specific amplification, showing a 163 bp target peak (corresponding to the primer pair AIV-M) and a 249 bp target peak (corresponding to the primer pair N1).

For the H3N6 subtype avian influenza virus, the primer combination achieved specific amplification, showing a 163 bp target peak (corresponding to the primer pair AIV-M) and a 240 bp target peak (corresponding to the primer pair N6).

For the H5N9 subtype avian influenza virus, the primer combination achieved specific amplification, showing a 163 bp target peak (corresponding to the primer pair AIV-M) and a 210 bp target peak (corresponding to the primer pair N9).

For the H7N7 subtype avian influenza virus, the primer combination achieved specific amplification, showing a 163 bp target peak (corresponding to the primer pair AIV-M) and a 198 bp target peak (corresponding to the primer pair N7).

For the H5N1 subtype avian influenza virus, the primer combination achieved specific amplification, showing a 163 bp target peak (corresponding to the primer pair AIV-M) and a 249 bp target peak (corresponding to the primer pair N1).

For the H7N9 subtype avian influenza virus, the primer combination achieved specific amplification, showing a 163 bp target peak (corresponding to the primer pair AIV-M) and a 210 bp target peak (corresponding to the primer pair N9).

For the H7N2 subtype avian influenza virus, the primer combination achieved specific amplification, showing a 163 bp target peak (corresponding to the primer pair AIV-M) and a 285 bp target peak (corresponding to the primer pair N2).

Example 4: Sensitivity of Primer Combination

I. Plasmid Construction

Using the cDNA samples of the H9N2 subtype avian influenza virus, the H5N1 subtype avian influenza virus, the H7N2 subtype avian influenza virus, the H2N3 subtype avian influenza virus, the H8N4 subtype avian influenza virus, the H12N5 subtype avian influenza virus, the H3N6 subtype avian influenza virus, the H7N7 subtype avian influenza virus, the H6N8 subtype avian influenza virus and the H7N9 subtype avian influenza virus obtained in step I of Example 2 as templates respectively, the full-length cDNA fragments of the M gene of the H9N2 subtype avian influenza virus, the NA gene of the H5N1 subtype Avian influenza virus, the NA gene of the H7N2 subtype avian influenza virus, the NA gene of the H2N3 subtype avian influenza virus, the NA gene of the H8N4 subtype avian influenza virus, the NA gene of the H12N5 subtype avian influenza virus, the NA gene of the H3N6 subtype avian influenza virus, the NA gene of the H7N7 subtype avian influenza virus, the NA gene of the H6N8 subtype avian influenza virus and the NA gene of the H7N9 subtype avian influenza virus were obtained by PCR amplification. These fragments were ligated to the pGEM-T EasyVector, respectively, and 10 recombinant plasmids pGEM-T-M, PGEM-T-N1, pGEM-T-N2, pGEM-T-N3, pGEM-T-N4, pGEM-T-N5, pGEM-T-N6, pGEM-T-N7, pGEM-T-N8 and pGEM-T-N9 were obtained. It was confirmed by sequencing that these 10 recombinant plasmids were inserted by the above genes, respectively, and these plasmids were standards for sensitivity tests.

II. Preparation of Template

The 10 plasmids prepared in step I were mixed to prepare template solutions. In template solution 1, the concentration of each of the 10 plasmids was $10^3$ copies/µL. In template solution 2, the concentration of each of the 10 plasmids was $10^2$ copies/µL. In template solution 3, the concentration of each of the 10 plasmids was $10^1$ copies/µL.

III. The Template Solutions Obtained in Step II were Taken as the Templates, GeXP Multiplex PCR was Performed with the Primer Combination.

The reaction system was the same as in Example 3.

The reaction procedure was the same as in Example 2.

IV. After Completing Step III, the Obtained PCR Products were Detected and Analyzed Using the GeXP System (GeXP Capillary Electrophoresis System).

Figure 1:
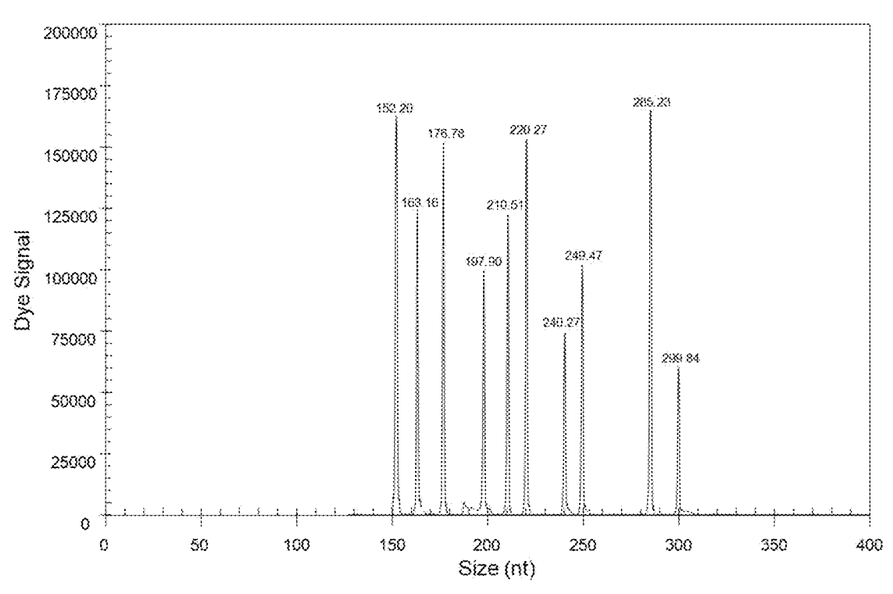
FIG. 1 shows a result of simultaneously detecting 10 target fragments in a 10-plex reaction system when the template solution 1 was used in Example 4.

The results showed that the $10^3$ copies/µL plasmid template and the $10^2$ copies/µL plasmid template could be detected, and most of the $10^1$ copies/µL plasmid template could not be detected. When template solution 1 was used, 10 target fragments were detected simultaneously in a 10-plex reaction system, and the result is shown in FIG. 1.

Example 5. Interference Test

I. Preparation of Template

In template solution 1, the concentration of the recombinant plasmid pGEM-T-N1 was $10^3$ copies/µL, and the concentration of the recombinant plasmid pGEM-T-N2 was $10^7$ copies/µL. In template solution 2, the concentration of the recombinant plasmid pGEM-T-N2 was $10^4$ copies/µL, the concentration of the recombinant plasmid pGEM-T-N7 was $10^2$ copies/µL, and the concentration of the recombinant plasmid pGEM-T-N9 was $10^6$ copies/µL. In template solution 3, the concentration of the recombinant plasmid pGEM-T-N3 was $10^3$ copies/µL, the concentration of the recombinant plasmid pGEM-T-N5 was $10^7$ copies/µL, the concentration of the recombinant plasmid pGEM-T-N6 was $10^5$ copies/µL, and the concentration of the recombinant plasmid pGEM-T-N8 was $10^2$ copies/µL.

II. Using the Template Solutions Obtained in Step I, GeXP Multiplex PCR was Performed with the Primer Combination.

The reaction system was the same as in Example 3.

The reaction procedure was the same as in Example 2.

III. After Completing Step II, the Obtained PCR Products were Detected and Analyzed Using the GeXP System (GeXP Capillary Electrophoresis System).

The corresponding target peaks appeared in all the samples and could be detected in both high concentration and low concentration templates with little interference, and there was no significant difference between the detected fluorescence signal values of multi-template and single-template.

Example 6. Stability Test

1. Intra-Batch Repeatability

Six repeated tests were performed on each test virus at the same time, and the methods were the same as in Example 3.

2. Inter-Batch Repeatability

Six repeated tests were performed on each test virus at different times, and the methods were the same as in Example 3.

The test results of intra-batch and inter-batch were consistent, and the stability was good.

Example 7. Comparative Primer

I. Comparative Experiment I

Primer pair N4-D was used instead of the primer pair N4, and the others were the same as in Example 3.

The Primer pair N4-D consists of the following forward primer and reverse primer (the predicted amplified fragment is 142 bp):

```
Forward primer:
AGGTGACACTATAGAATAAGATCGGYTATRTATGTAGTGG;

Reverse primer:
GTACGACTCACTATAGGGACCATATCTDCCYTTCCCATT.
```

The target peaks of the primer pair N2 and the primer pair N5 could not be detected effectively.

II. Comparative Experiment II

Primer pair N3-D was used instead of the primer pair N3, and the others were the same as in Example 3.

The Primer pair N3-D consists of the following forward primer and reverse primer (the predicted amplified fragment is 147 bp):

```
Forward primer:
AGGTGACACTATAGAATACTGGAAACAGGGTATGTATG;

Reverse primer:
GTACGACTCACTATAGGGAGTCAATGGAGGACCYGGAGT.
```

The target peaks of the primer pair N5 and the primer pair N6 could not be detected effectively.

III. Comparative Experiment III

Primer pair AIV-M-D was used instead of the primer pair AIV-M, primer pair N4-D was used instead of the primer pair N4, and primer pair N7-D was used instead of the primer pair N7 and the others were the same as in Example 3.

The primer pair AIV-M-D consists of the following forward primer and reverse primer (predicted amplified fragment is 263 bp):

```
Forward primer:
AGGTGACACTATAGAATATGCCCAGTGAGCGAGGACTG;

Reverse primer:
GTACGACTCACTATAGGGAGCCACTTCTGTGGTCACCGT.
```

The primer pair N4-D consists of the following forward primer and reverse primer (the predicted amplified fragment is 154 bp):

```
Forward primer:
AGGTGACACTATAGAATAGGATGCWAATGGRTGGGTGTC;

Reverse primer:
GTACGACTCACTATAGGGAACCGGTTGTTTCTCCTCTAAT.
```

The primer pair N7-D consists of the following forward primer and reverse primer (the predicted amplified fragment is 199 bp):

```
Forward primer:
AGGTGACACTATAGAATAGAGTTTATGCAAAGTTGAAGG;

Reverse primer:
GTACGACTCACTATAGGGAGTTTCTAATGGTWGTCCCTTG.
```

The target peaks of the primer pair N1, the primer pair N3, the primer pair N5, and the primer pair N6 could not be detected effectively.

INDUSTRIAL APPLICATIONS

In order to establish a GeXP detection method for simultaneously identifying 9 NA subtypes of avian influenza, the inventors of the present invention have provided 10 specific primer pairs, and performed specificity, sensitivity, interference, stability verification and clinical sample testing on a multiplex reaction system of a primer combination consisting of the 10 primer pairs. The 10-plex reaction system all can amplify a template which comprises a single nucleic acid, several randomly mixed nucleic acids, or nine mixed nucleic acids, which is consistent with the expected design. Specificity is strong, and there is no cross-reaction to common poultry pathogens such as Newcastle disease virus and infectious bronchitis virus, etc. The detection threshold for the simultaneous identification of 10 target genes is $10^2$ copies/μL. Simultaneous detection of different templates with different concentrations is not significantly different from the detection of a single template, indicating that the interference between the 10 primer pairs is small. The tests of the same template at the same time and at different times show good repeatability and stability. The GeXP detection method in combination with the primer combination provided by the present invention can perform 10-plex PCR amplification in the same reaction system, effectively identify 9 NA subtypes, and has the advantages of high throughput, fast, time-saving and labor-saving. The present invention provides an effective method for rapid identification of 9 different NA subtype AIVs and has a broad application prospect.

What is claimed is:

1. A primer combination, comprising the following 10 primer pairs:
   primer pair AIV-M, which consists of a forward primer and a reverse primer,
   wherein the forward primer comprises a nucleotide sequence of positions 19-38 of SEQ ID NO: 1, and
   wherein the reverse primer comprises a nucleotide sequence of positions 20-39 of SEQ ID NO: 2,
   primer pair N1, which consists of a forward primer and a reverse primer,
   wherein the forward primer comprises a nucleotide sequence of positions 19-38 of SEQ ID NO: 3, and
   wherein the reverse primer comprises a nucleotide sequence of positions 20-38 of SEQ ID NO: 4 ,
   primer pair N2, which consists of a forward primer and a reverse primer,
   wherein the forward primer comprises a nucleotide sequence of positions 19-35 of SEQ ID NO: 5, and
   wherein the reverse primer comprises a nucleotide sequence of positions 20-36 of SEQ ID NO: 6 ,
   primer pair N3, which consists of a forward primer and a reverse primer,
   wherein the forward primer comprises a nucleotide sequence of positions 19-41 of SEQ ID NO: 7, and
   wherein the reverse primer comprises a nucleotide sequence of positions 20-41 of SEQ ID NO: 8 of the Sequence Listing,
   primer pair N4, which consists of a forward primer and a reverse primer,
   wherein the forward primer comprises a nucleotide sequence of positions 19-40 of SEQ ID NO: 9, and
   wherein the reverse primer comprises a nucleotide sequence of positions 20-39 of SEQ ID NO: 10 ,
   primer pair N5, which consists of a forward primer and a reverse primer,
   wherein the forward primer comprises a nucleotide sequence of positions 19-38 of SEQ ID NO: 11, and
   wherein the reverse primer comprises a nucleotide sequence of positions 20-40 of SEQ ID NO: 12 ,
   primer pair N6, which consists of a forward primer and a reverse primer,
   wherein the forward primer comprises a nucleotide sequence of positions 19-43 of SEQ ID NO: 13, and
   wherein the reverse primer comprises a nucleotide sequence of positions 20-44 of SEQ ID NO: 14 ,
   primer pair N7, which consists of a forward primer and a reverse primer,
   wherein the forward primer comprises a nucleotide sequence of positions 19-38 of SEQ ID NO: 15, and
   wherein the reverse primer comprises a nucleotide sequence of positions 20-39 of SEQ ID NO: 16 ,
   primer pair N8, which consists of a forward primer and a reverse primer,
   wherein the forward primer comprises a nucleotide sequence of positions 19-38 of SEQ ID NO: 17, and
   wherein the reverse primer comprises a nucleotide sequence of positions 20-40 of SEQ ID NO: 18, and;
   primer pair N9, which consists of a forward primer and a reverse primer,
   wherein the forward primer comprises a nucleotide sequence of positions 19-39 of SEQ ID NO: 19, and
   wherein the reverse primer comprises a nucleotide sequence of positions 20-39 of SEQ ID NO: 20,
   wherein, each forward primer of the 10 primer pairs further comprising a 5' end upstream GeXP universal primer, and each reverse primer of the 10 primer pairs further comprising a 5' end upstream GeXP universal primer.

2. The primer combination according to claim 1, wherein,
   primer pair AIV-M, comprising a forward primer with the nucleotide sequence set forth in SEQ ID NO: 1, and a reverse primer with the nucleotide sequence set forth in SEQ ID NO: 2 ,
   primer pair N1, comprising a forward primer with the nucleotide sequence set forth in SEQ ID NO: 3, and a reverse primer with the nucleotide sequence set forth in SEQ ID NO: 4 ,
   primer pair N2, comprising a forward primer with the nucleotide sequence set forth in SEQ ID NO: 5, and a reverse primer with the nucleotide sequence set forth in SEQ ID NO: 6 ,
   primer pair N3, comprising a forward primer with the nucleotide sequence set forth in SEQ ID NO: 7, and a reverse primer with the nucleotide sequence set forth in SEQ ID NO: 8 ,
   primer pair N4, comprising a forward primer with the nucleotide sequence set forth in SEQ ID NO: 9, and a reverse primer with the nucleotide sequence set forth in SEQ ID NO: 10 ,
   primer pair N5, comprising a forward primer with the nucleotide sequence set forth in SEQ ID NO: 11, and a reverse primer with the nucleotide sequence set forth in SEQ ID NO: 12 ;

primer pair N6, comprising a forward primer with the nucleotide sequence set forth in SEQ ID NO: 13, and a reverse primer with the nucleotide sequence set forth in SEQ ID NO: 14, primer pair N7, comprising a forward primer with the nucleotide sequence set forth in SEQ ID NO: 15, and a reverse primer with the nucleotide sequence set forth in SEQ ID NO: 16, primer pair N8, comprising a forward primer with the nucleotide sequence set forth in SEQ ID NO: 17, and a reverse primer with the nucleotide sequence set forth in SEQ ID NO: 18;

primer pair N9, comprising a forward primer with the nucleotide sequence set forth in SEQ ID NO: 19, and a reverse primer with the nucleotide sequence set forth in SEQ ID NO: 20.

3. A method, comprising the following steps:

performing multiplex PCR with the cDNA of a sample to be tested as a template and the primer combination according to claim 1, to generate an amplification product;

detecting the amplification product; and determining whether the sample contains avian influenza virus and what subtype of the avian influenza virus is present.

4. The primer combination according to claim 1, wherein the molar quantities of various primers are equal.

5. The method according to claim 3, wherein;

if the amplification product contains a 163 bp±3 bp DNA fragment, it is determined that the sample contains an avian influenza virus;

if the amplification product contains a 249 bp±3 bp DNA fragment, it is determined that the sample contains a N1 subtype avian influenza virus;

if the amplification product contains a 285 bp±3 bp DNA fragment, it is determined that the sample contains a N2 subtype avian influenza virus;

if the amplification product contains a 220 bp±3 bp DNA fragment, it is determined that the sample contains a N3 subtype avian influenza virus;

if the amplification product contains a 152 bp±3 bp DNA fragment, it is determined that the sample contains a N4 subtype avian influenza virus;

if the amplification product contains a 300 bp±3 bp DNA fragment, it is determined that the sample contains a N5 subtype avian influenza virus;

if the amplification product contains a 240 bp±3 bp DNA fragment, it is determined that the sample contains a N6 subtype avian influenza virus;

if the amplification product contains a 198 bp±3 bp DNA fragment, it is determined that the sample contains a N7 subtype avian influenza virus;

if the amplification product contains a 177 bp±3 bp DNA fragment, it is determined that the sample contains a N8 subtype avian influenza virus; and if the amplification product contains a 210 bp±3 bp DNA fragment, it is determined that the sample contains a N9 subtype avian influenza virus.

* * * * *

SEQUENCE LISTING

```
<160> NUMBER OF SEQ ID NOS: 30

<210> SEQ ID NO 1
<211> LENGTH: 38
<212> TYPE: DNA
<213> ORGANISM: Artificial Sequence
<220> FEATURE:
<223> OTHER INFORMATION: Synthesized

<400> SEQUENCE: 1
aggtgacact atagaataag gctctcatgg agtggcta                          38

<210> SEQ ID NO 2
<211> LENGTH: 39
<212> TYPE: DNA
<213> ORGANISM: Artificial Sequence
<220> FEATURE:
<223> OTHER INFORMATION: Synthesized

<400> SEQUENCE: 2
gtacgactca ctatagggat ggacaaagcg tctacgctg                         39
```

<210> SEQ ID NO 3
<211> LENGTH: 38
<212> TYPE: DNA
<213> ORGANISM: Artificial Sequence
<220> FEATURE:
<223> OTHER INFORMATION: Synthesized

<400> SEQUENCE: 3
aggtgacact atagaatagg tgtttggatc ggragaac         38

<210> SEQ ID NO 4
<211> LENGTH: 38
<212> TYPE: DNA
<213> ORGANISM: Artificial Sequence
<220> FEATURE:
<223> OTHER INFORMATION: Synthesized

<400> SEQUENCE: 4
gtacgactca ctatagggat caacccagaa rcaaggtc         38

<210> SEQ ID NO 5
<211> LENGTH: 35
<212> TYPE: DNA
<213> ORGANISM: Artificial Sequence
<220> FEATURE:
<223> OTHER INFORMATION: Synthesized

<400> SEQUENCE: 5
aggtgacact atagaatatt gggtgttccg tttca            35

<210> SEQ ID NO 6
<211> LENGTH: 36
<212> TYPE: DNA
<213> ORGANISM: Artificial Sequence
<220> FEATURE:
<223> OTHER INFORMATION: Synthesized

<400> SEQUENCE: 6
gtacgactca ctatagggac catccgtcat tactac           36

<210> SEQ ID NO 7
<211> LENGTH: 41
<212> TYPE: DNA
<213> ORGANISM: Artificial Sequence
<220> FEATURE:
<223> OTHER INFORMATION: Synthesized

<400> SEQUENCE: 7
aggtgacact atagaatatt cccaatagga acagcyccag t     41

<210> SEQ ID NO 8
<211> LENGTH: 41
<212> TYPE: DNA
<213> ORGANISM: Artificial Sequence
<220> FEATURE:
<223> OTHER INFORMATION: Synthesized

<400> SEQUENCE: 8
gtacgactca ctatagggat tctccatgat ttratggagt c     41

<210> SEQ ID NO 9
<211> LENGTH: 40
<212> TYPE: DNA
<213> ORGANISM: Artificial Sequence
<220> FEATURE:

```
<223> OTHER INFORMATION: Synthesized

<400> SEQUENCE: 9
aggtgacact atagaataca gayaaggayt caaatggtgt                    40

<210> SEQ ID NO 10
<211> LENGTH: 39
<212> TYPE: DNA
<213> ORGANISM: Artificial Sequence
<220> FEATURE:
<223> OTHER INFORMATION: Synthesized

<400> SEQUENCE: 10
gtacgactca ctatagggac atggtacagt gcaattcct                     39

<210> SEQ ID NO 11
<211> LENGTH: 38
<212> TYPE: DNA
<213> ORGANISM: Artificial Sequence
<220> FEATURE:
<223> OTHER INFORMATION: Synthesized

<400> SEQUENCE: 11
aggtgacact atagaatagt gaggtcatgg agaaagca                      38

<210> SEQ ID NO 12
<211> LENGTH: 40
<212> TYPE: DNA
<213> ORGANISM: Artificial Sequence
<220> FEATURE:
<223> OTHER INFORMATION: Synthesized

<400> SEQUENCE: 12
gtacgactca ctatagggat ggyctattca ttccrttcca                    40

<210> SEQ ID NO 13
<211> LENGTH: 43
<212> TYPE: DNA
<213> ORGANISM: Artificial Sequence
<220> FEATURE:
<223> OTHER INFORMATION: Synthesized

<400> SEQUENCE: 13
aggtgacact atagaataca ctatagatcc ygaratgatg acc                43

<210> SEQ ID NO 14
<211> LENGTH: 44
<212> TYPE: DNA
<213> ORGANISM: Artificial Sequence
<220> FEATURE:
<223> OTHER INFORMATION: Synthesized

<400> SEQUENCE: 14
gtacgactca ctatagggag gagtctttgc taatwgtcct tcca               44

<210> SEQ ID NO 15
<211> LENGTH: 38
<212> TYPE: DNA
<213> ORGANISM: Artificial Sequence
<220> FEATURE:
<223> OTHER INFORMATION: Synthesized

<400> SEQUENCE: 15
aggtgacact atagaataga cagracwgct ttcagagg                      38
```

<210> SEQ ID NO 16
<211> LENGTH: 39
<212> TYPE: DNA
<213> ORGANISM: Artificial Sequence
<220> FEATURE:
<223> OTHER INFORMATION: Synthesized

<400> SEQUENCE: 16
gtacgactca ctatagggag ttgcgttgtc attatttcc          39

<210> SEQ ID NO 17
<211> LENGTH: 38
<212> TYPE: DNA
<213> ORGANISM: Artificial Sequence
<220> FEATURE:
<223> OTHER INFORMATION: Synthesized

<400> SEQUENCE: 17
aggtgacact atagaataag ggaatacaat gaaacagt           38

<210> SEQ ID NO 18
<211> LENGTH: 40
<212> TYPE: DNA
<213> ORGANISM: Artificial Sequence
<220> FEATURE:
<223> OTHER INFORMATION: Synthesized

<400> SEQUENCE: 18
gtacgactca ctagggat gcaaaaccct tagcatcaca           40

<210> SEQ ID NO 19
<211> LENGTH: 39
<212> TYPE: DNA
<213> ORGANISM: Artificial Sequence
<220> FEATURE:
<223> OTHER INFORMATION: Synthesized

<400> SEQUENCE: 19
aggtgacact atagaatacg ccctgataag ctggccact          39

<210> SEQ ID NO 20
<211> LENGTH: 39
<212> TYPE: DNA
<213> ORGANISM: Artificial Sequence
<220> FEATURE:
<223> OTHER INFORMATION: Synthesized

<400> SEQUENCE: 20
gtacgactca ctagggaa caggccttct gttgtacca             39

<210> SEQ ID NO 21
<211> LENGTH: 40
<212> TYPE: DNA
<213> ORGANISM: Artificial Sequence
<220> FEATURE:
<223> OTHER INFORMATION: Synthesized

<400> SEQUENCE: 21
aggtgacact atagaataag atcggytatr tatgtagtgg          40

<210> SEQ ID NO 22
<211> LENGTH: 39
<212> TYPE: DNA
<213> ORGANISM: Artificial Sequence
<220> FEATURE:
<223> OTHER INFORMATION: Synthesized

<400> SEQUENCE: 22
gtacgactca ctatagggac catatctdcc yttcccatt                39

<210> SEQ ID NO 23
<211> LENGTH: 38
<212> TYPE: DNA
<213> ORGANISM: Artificial Sequence
<220> FEATURE:
<223> OTHER INFORMATION: Synthesized

<400> SEQUENCE: 23
aggtgacact atagaatact ggaaacaggg tatgtatg                 38

<210> SEQ ID NO 24
<211> LENGTH: 39
<212> TYPE: DNA
<213> ORGANISM: Artificial Sequence
<220> FEATURE:
<223> OTHER INFORMATION: Synthesized

<400> SEQUENCE: 24
gtacgactca ctatagggag tcaatggagg accyggagt                39

<210> SEQ ID NO 25
<211> LENGTH: 38
<212> TYPE: DNA
<213> ORGANISM: Artificial Sequence
<220> FEATURE:
<223> OTHER INFORMATION: Synthesized

<400> SEQUENCE: 25
aggtgacact atagaatatg cccagtgagc gaggactg                 38

<210> SEQ ID NO 26
<211> LENGTH: 39
<212> TYPE: DNA
<213> ORGANISM: Artificial Sequence
<220> FEATURE:
<223> OTHER INFORMATION: Synthesized

<400> SEQUENCE: 26
gtacgactca ctatagggag ccacttctgt ggtcaccgt                39

<210> SEQ ID NO 27
<211> LENGTH: 39
<212> TYPE: DNA
<213> ORGANISM: Artificial Sequence
<220> FEATURE:
<223> OTHER INFORMATION: Synthesized

<400> SEQUENCE: 27
aggtgacact atagaatagg atgcwaatgg rtgggtgtc                39

<210> SEQ ID NO 28
<211> LENGTH: 40
<212> TYPE: DNA
<213> ORGANISM: Artificial Sequence
<220> FEATURE:
<223> OTHER INFORMATION: Synthesized

<400> SEQUENCE: 28
gtacgactca ctatagggaa ccggttgttt ctcctctaat               40

<210> SEQ ID NO 29
<211> LENGTH: 39

```
<212> TYPE: DNA
<213> ORGANISM: Artificial Sequence
<220> FEATURE:
<223> OTHER INFORMATION: Synthesized

<400> SEQUENCE: 29
aggtgacact atagaataga gtttatgcaa agttgaagg                    39

<210> SEQ ID NO 30
<211> LENGTH: 40
<212> TYPE: DNA
<213> ORGANISM: Artificial Sequence
<220> FEATURE:
<223> OTHER INFORMATION: Synthesized

<400> SEQUENCE: 30
gtacgactca ctatagggag tttctaatgg twgtcccttg                   40
```